United States Patent [19]
Olesen et al.

[11] Patent Number: 6,083,957
[45] Date of Patent: *Jul. 4, 2000

[54] HETEROCYCLIC COMPOUNDS AND THEIR PREPARATION AND USE

[75] Inventors: Preben H. Olesen, Copenhagen; Per Sauerberg, Farum, both of Denmark

[73] Assignee: Novo Nordisk A/S, Bagsvaerd, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/839,289

[22] Filed: Apr. 17, 1997

[30] Foreign Application Priority Data

Apr. 24, 1996 [DK] Denmark .................. 0493/96

[51] Int. Cl.[7] ............... A61K 31/439; C07D 453/00; C07D 453/02; C07D 417/04
[52] U.S. Cl. ............... 514/305; 514/210; 514/340; 514/342; 546/133; 546/268.7; 546/269.4; 540/362
[58] Field of Search ............. 514/305, 340, 514/342, 210; 546/133, 268.7, 269.4; 540/362

[56] References Cited

U.S. PATENT DOCUMENTS

| | | | |
|---|---|---|---|
| 5,041,455 | 8/1991 | Sauerberg et al. | 514/342 |
| 5,260,314 | 11/1993 | Sauerberg et al. | 514/305 |
| 5,488,056 | 1/1996 | Bodick et al. | 514/305 |

FOREIGN PATENT DOCUMENTS

| | | |
|---|---|---|
| 0 296 721 | 12/1988 | European Pat. Off. |
| 0 307 142 | 3/1989 | European Pat. Off. |
| 0 384 288 | 8/1990 | European Pat. Off. |
| WO 92/03430 | 3/1992 | WIPO |
| WO 92/03431 | 3/1992 | WIPO |
| WO 92/03433 | 3/1992 | WIPO |
| WO 94/20496 | 9/1994 | WIPO |

OTHER PUBLICATIONS

Saunders, J. et al, J. Med. Chem., 1990, 33, pp. 1128–1138.
Morrison, R.T. et al, Organic Chemistry, 4th edition, Allyn & Bacon Inc., 1983, p. 919.

Primary Examiner—Alan L. Rotman
Attorney, Agent, or Firm—Steve T. Zelson, Esq.; Elias J. Lambiris, Esq.

[57] ABSTRACT

The present invention relates to therapeutically active quaternary azacyclic or azabicyclic compounds with formula I:

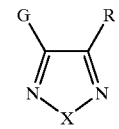

wherein X is oxygen or sulfur and wherein G is selected from the group of azacyclic or azabicyclic ring systems consisting of:

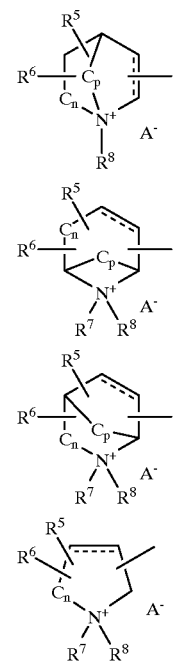

a method of preparing the same and to pharmaceutical compositions comprising the compounds. The novel compounds are useful in treating a cholinergic deficit in the peripheral system.

24 Claims, No Drawings

HETEROCYCLIC COMPOUNDS AND THEIR PREPARATION AND USE

CROSS-REFERENCE TO RELATED APPLICATIONS

This application claims priority under 35 U.S.C. 119 of Danish application 0493/96 filed Apr. 24, 1996, the contents of which are fully incorporated herein by reference.

The present invention relates to therapeutically active quaternary azacyclic and azabicyclic compounds, a method of preparing the same and to pharmaceutical compositions comprising the compounds.

The novel compounds are useful as stimulants in the peripheral cholinergic system or for treatment of a cholinergic deficit in the peripheral system.

From basic pharmacology it is known that cholinergic agonists effect the cardiovascular system, the gastrointestinal system, and the urinary tract. They also stimulate secretion by exocrine glands that receive parasymphatic innervation and that include the lacrimal, tracheobronchial, salivary, digestive and sweat glands. Cholinergic agonists also evoke bronchoconstriction and when instilled to the eye produce miosis.

The recent elucidations of the existence and distinct tissue distribution of several subtypes of muscarinic cholinergic receptors has renewed interest in synthetic analogs that enhance the tissue selectivety of muscarinic agonist.

It is an object of the invention to provide new muscarinic cholinergic compounds for treatment of glaucoma, gastrointestinal motility disorders, irritable bowel syndrome (IBS), urinary bladder disorders and respiratory disorders.

The novel compounds of the invention are quaternary compounds of formula I:

(I)

wherein X is oxygen or sulfur and wherein G is selected from the group of azacyclic or azabicyclic ring systems consisting of:

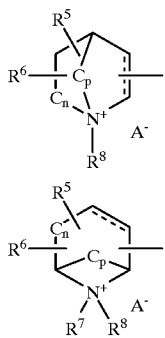

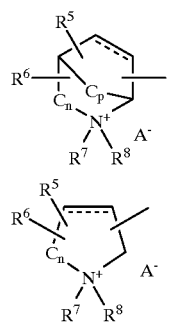

wherein the oxadiazole or thiadiazole ring can be attached at any position; and $R^5$ and $R^6$ may be present at any possible position, including the point of attachment of the oxadiazole or thiadiazole ring, and independently are H, straight or branched $C_{1-5}$-alkyl, straight or branched $C_{2-5}$-alkenyl, straight or branched $C_{2-5}$-alkynyl, straight or branched $C_{1-10}$-alkoxy, straight or branched hydroxyalkyl, —OH, halogen, —NH$_2$ or carboxy; and $R^7$ and $R^8$ independently are straight or branched $C_{1-5}$-alkyl, straight or branched $C_{2-5}$-alkenyl, straight or branched $C_{2-5}$-alkynyl, $C_{3-5}$-cycloalkyl or $C_{3-5}$-cycloalkylC$_{1-2}$-alkyl; and n and p independently are 0, 1, 2, 3, or 4; and . . . is a single or double bond; and R is hydrogen, halogen, —NR$^1$R$^2$, —R$^3$, —OR$^3$, —SR$^3$, —SOR$^3$, —SO$_2$R$^3$, $C_{3-8}$-cycloalky, $C_{4-12}$-(cycloalkylalkyl), —Z—C$_{3-10}$-cycloalkyl and —Z—C$_{4-12}$-(cycloalkylalkyl) wherein R$^3$ is straight or branched $C_{1-5}$-alkyl, straight or branched $C_{2-15}$-alkenyl, straight or branched $C_{2-15}$-alkynyl, or straight or branched $C_{4-15}$-alkenynyl, each of which is optionally substituted with one or more halogen(s), —CF$_3$, —CN, —OH, Y, phenyl or phenoxy wherein phenyl or phenoxy is optionally substituted with halogen, —OH, —CF$_3$, —CN, $C_{1-4}$-alkyl, $C_{1-4}$-alkoxy, $C_{1-4}$-alkylthio, —SCF$_3$, —OCF$_3$, —CONH$_2$ or —CSNH$_2$; or R is phenyl or benzyloxycarbonyl, each of which is optionally substituted with halogen, —OH, —CF$_3$, —CN, $C_{1-4}$-alkyl, $C_{1-4}$-alkoxy, $C_{1-4}$-alkylthio, —SCF$_3$, —OCF$_3$, —CONH$_2$ or —CSNH$_2$; or R is —OR$^4$Y, —SR$^4$Y, —OR$^4$ZY, —SR$^4$ZY, —OR$^4$ZR$^3$ or —SR$^4$ZR$^3$ wherein Z is oxygen or sulphur, R$^4$ is straight or branched $C_{1-15}$-alkylene, straight or branched $C_{2-15}$-alkenylene, straight or branched $C_{2-15}$-alkynylene or straight or branched $C_{4-15}$-alkenynylene; and Y is a 5 or 6 membered heterocyclic group, which heterocyclic group is optionally substituted at carbon or nitrogen atom(s) with halogen,—OH, —CF$_3$, —CN, $C_{1-4}$-alkyl, $C_{1-4}$-alkoxy, $C_{1-4}$-alkylthio, —SCF$_3$, —OCF$_3$, —CONH$_2$, —CSNH$_2$, phenyl, benzyl or thienyl, or a carbon atom in the heterocyclic group together with an oxygen atom form a carbonyl group, or which heterocyclic group is optionally fused with a phenyl group; and $R^1$ and $R^2$ independently are hydrogen, $C_{1-6}$-alkyl, or $R^1$ and $R^2$ together with the nitrogen atom optionally form a 4- to 6-membered ring; and A is a negative radical of a pharmaceutically acceptable salt; or a pharmaceutically acceptable salt thereof with a pharmaceutically acceptable acid or a prodrug thereof.

As used herein, the term "halogen" means F, Cl, Br, and I. Especially preferred halogens include Cl, Br, and F.

The term "$C_{1-n'}$-alkyl" wherein n' can be from 2 through 15, as used herein, represent a branched or straight alkyl group having from one to the specified number of carbon atoms. Typical $C_{1-6}$-alkyl groups include, but are not limited to, methyl, ethyl, n-propyl, iso-propyl, butyl, iso-butyl, sec-butyl, tert-butyl, pentyl, hexyl and the like.

The term "$C_{2-n'}$-alkenyl" wherein n' can be from 3 through 15, as used herein, represents an olefinically unsaturated branched or straight group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_{2-n'}$-alkynyl" wherein n' can be from 3 through 15, as used herein, represent an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The term "$C_{4-n'}$-alkenynyl" wherein n' can be from 5 through 15, as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like.

The term "$C_{3-n}$-cycloalkyl" wherein n=4–10, as used herein, represents e.g. cyclopropyl, cyclobutyl, cyclopentyl, cyclohexyl, cycloheptyl and cyclooctyl and the like.

As used herein the term "$C_{4-12}$-(cycloalkylalkyl)" represents a branched or straight alkyl group substituted at a carbon with a cycloalkyl group. Examples of such groups include, but are not limited to, cyclopropylethyl, cyclobutylmethyl, 2-(cyclohexyl)ethyl, cyclohexylmethyl, 3-(cyclopentyl)-1-propyl, and the like.

The term "$C_{1-n''}$-alkoxy" wherein n'' can be from 2 through 10, as used herein, alone or in combination, refers to a straight or branched monovalent substituent comprising an alkyl group having from one to the specified number of carbon atoms linked through an ether oxygen having its free valence bond from the ether oxygen. Examples of such groups include, but are not limited to, e.g. methoxy, ethoxy, propoxy, isopropoxy, butoxy and the like.

The term "$C_{1-n''}$-alkylthio" wherein n'' can be from 2 through 10, as used herein, alone or in combination, refers to a straight or branched monovalent substituent comprising an alkyl group having from one to the specified number of carbon atoms linked through a divalent sulfur atom having its free valence bond from the sulfur oxygen. Examples of such groups include, but are not limited to, e.g. methylthio, ethylthio, propylthio, isopropylthio, butylthio and the like.

As used herein, the phrase "$R^1$ and $R^2$ together with the nitrogen atom optionally form a 4- to 6-membered ring" for example, include, but are not limited to:

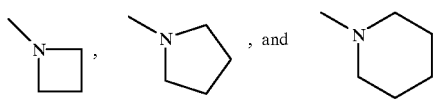

As used herein, the phrase "5 or 6 membered heterocyclic group" means a group containing from one to four N, O or S atom(s) or a combination thereof, which heterocyclic group is optionally substituted at carbon or nitrogen atom(s) with halogen, —OH, —$CF_3$, —CN, $C_{1-4}$-alkyl, $C_{1-4}$-alkoxy, $C_{1-4}$-alkylthio, —$SCF_3$, —$OCF_3$, —$CONH_2$, —$CSNH_2$, phenyl, benzyl or thienyl, or a carbon atom in the heterocyclic group together with an oxygen atom form a carbonyl group, or which heterocyclic group is optionally fused with a phenyl group. The phrase "5 or 6 membered heterocyclic group" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having four heteroatoms; 6-membered heterocycles with one heteroatom (e.g. pyridine, quinoline, isoquinoline, phenanthridine, cyclohepta[b]pyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-membered heterocycles with four heteroatoms. Particularly preferred are thiophenes, pyridines, and furans, more preferred is thiophenes.

As used herein the term "carboxy" refers to a substituent having the common meaning understood by the skilled artisan, wherein the point of attachment may be through the carbon or oxygen atom of the group.

As used herein, the phrase "one or more selected from" shall more preferably refer to from 1–3 substituents. The term shall further preferably refer to from 1–2 substituents.

In a preferred embodiment, the present invention is concerned with compounds of formula I wherein G is selected from:

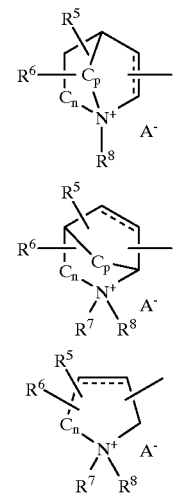

and wherein n, p, $R^5$, $R^{6,}$ $R^7$, $R^8$ and $A^-$ are as defined above.

In another preferred embodiment, the present invention is concerned with compounds of formula I wherein G is selected from:

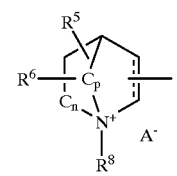

-continued

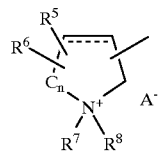

and wherein n, p, $R^5$, $R^6$, $R^7$, $R^8$ and $A^-$ are as defined above.

In another preferred embodiment, the present invention is concerned with compounds of formula I wherein n is 1 or 2.

In another preferred embodiment, the present invention is concerned with compounds of formula I wherein p is 1 or 2.

In another preferred embodiment, the present invention is concerned with compounds of formula I wherein R is halogen, —$OR^3$, —$SR^3$ or —$SO_2R^3$, wherein $R^3$ is as defined above.

In another preferred embodiment, the present invention is concerned with compounds of formula I wherein $R^3$ is straight or branched $C_{1-15}$-alkyl, straight or branched $C_{2-15}$-alkenyl, straight or branched $C_{2-15}$-alkynyl or straight or branched $C_{4-15}$-alkenynyl, each of which is optionally substituted with one or more halogen(s), —CN, —$SCF_3$, —$OCF_3$, Y or phenyl, wherein phenyl or Y is optionally substituted with halogen(s), —CN, $C_{1-4}$-alkyl, $C_{1-4}$-alkoxy, $C_{1-4}$-alkylthio, —$SCF_3$ or —$OCF_3$.

In another preferred embodiment, the present invention is concerned with compounds of formula I wherein R is —$OR^3$ or —$SR^3$, wherein $R^3$ is propynyl substituted with phenyl or thienyl, wherein phenyl or thienyl is optionally substituted with halogen(s), —CN, $C_{1-4}$-alkyl, $C_{1-4}$-alkoxy, $C_{1-4}$-alkylthio, —$SCF_3$ or —$OCF_3$.

In another preferred embodiment, the present invention is concerned with compounds of formula I wherein the oxadiazole or thiadiazole is attached at the 3 position of G.

In another preferred embodiment, the present invention is concerned with compounds of formula I wherein $R^5$ and $R^6$ are H.

In another preferred embodiment, the present invention is concerned with compounds of formula I wherein $R^7$ is $C_{1-2}$-alkyl.

In another preferred embodiment, the present invention is concerned with compounds of formula I wherein $R^8$ is $C_{1-2}$-alkyl.

It is to be understood that the invention extends to each of any of the stereoisomeric forms of the compounds of the present invention as well as the pure diastereomeric, pure enantiomeric, and racemic forms of the compounds of this invention.

The starting materials for the illustrated process are, if nothing else mentioned, commercially available or may be prepared using methods known to the skilled artisan.

Pharmaceutical salts suitable as acid addition salts and also as providing the anions of cyclic amine salts are those from acids such as hydrochloric, hydrobromic, hydroiodic, phosphoric, sulfuric, triflouracetic, trichloracetic, oxalic, maleic, pyruvic, malonic, succinic, citric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference.

The invention also relates to methods of preparing the above mentioned compounds, characterized in:

reacting a compound of formula II:

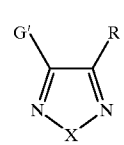

(II)

(prepared according to methods described in EP 384288, PCT/DK91/00234, PCT/DK91/00235 and PCT/DK91/00236) wherein G' is selected from the azacyclic or azabicyclic ring systems consisting of:

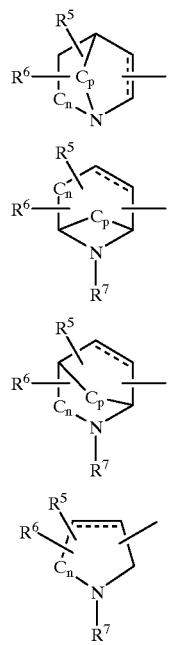

wherein X, R, $R^5$, $R^6$, $R^7$, $C_n$ and $C_p$ have the meanings defined above with an active quaternizing agent of the formula $R^8L$ wherein $R^8$ has the meaning defined above and L is a leaving group (e.g. a halogen ion), whereafter L optionally can be exhanged with A which is as defined above e.g. by ion exhange to give compounds of formula I.

It is to be understood that the invention extends to each of the stereoisomeric forms of the compounds of formula I as well as the racemates.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

The inhibitory effects of compounds on $^3$H-Oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min. at 40,000×g. The pellet is washed three times with buffer. In each step the pellet is homogenized as before in 2×10 ml of buffer and centrifuged for 10 min. at 40,000×g.

The final pellet is homogenized in 20 mM Hepes pH: 7.4 (100 ml per g of original tissue) and used for binding assay. Aliquots of 0.5 ml is added 25 ul of test solution and 25 ul of $^3$H-Oxotremorine (1.0 nM, final concentration) mixed and incubated for 30 min. at 25° C. Non-specific binding is determined in triplicate using arecoline (1 ug/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steam-bath for less than 5 min.) at a concentration of 2.2 mg/ml. 25–75% inhibition of specific binding must be obtained before calculation of $IC_{50}$.

The test value will be given as $IC_{50}$ (the concentration (nM) of the test substance which inhibits the specific binding of $^3$H-Oxo by 50%).

$IC_{50}$=(applied test substance concentration)

$$x \frac{1}{\left(\frac{C_o}{C_x}\right)} nM$$

where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$H-PRZ (pirenzepine, [N-methyl-$^3$H]) binding to rat cerebral cortex membranes.

Pirenzepine binds selectively to subtype of muscarinic receptors. Historically the type is named the $M_1$-site, whereas pirenzepine sensitive site would be more appropriate. Although selective for $M_1$-sites pirenzepine also interact with $M_2$-sites.

All preparations are performed at 0–4° C. unless otherwise indicated. Fresh cortex (0.1–1 g) from male Wistar rats (150–200 g) is homogenized for 5–10 s. in 10 ml 20 mM Hepes pH: 7.4, with an Ultra-Turrax homogenizer. The homogenizer is rinzed with 2×10 ml of buffer and the combined suspension centrifuged for 15 min at 40,000 xg. The pellet is washed three times with buffer. In each step the pellet is homogenized as before in 3×10 ml of buffer and centrifuged for 10 min at 40,000 xg.

The final pellet is homogenized in 20 mM Hepes pH: 7.4 (100 ml per g of original tissue) and used for binding assay. Aliquots of 0.5 ml is added 20 μl of test solution and 25 μl of $^3$H-Pirenzepine (1.0 nM, final conc.), mixed and incubated for 60 min at 20° C. Non-specific binding is determined in triplicate using atropine (1 μg/ml, final conc.) as the test substance. After incubation samples are added 5 ml of ice-cold buffer and poured directly onto Whatman GF/C glass fiber filters inder suction and immediately washed 2 times with 5 ml of ice-cold buffer. The amount of radioactivity on the filters are determined by conventional liquid scintillation counting. Specific binding is total binding minus non-specific binding.

Test substances are dissolved in 10 ml water, at a concentration of 0.22 mg/ml. 25–75% inhibition of specific binding must be obtained before calculation of $IC_{50}$.

The test value will be given as $IC_{50}$ (the concentration, nM) of the test substance which inhibits the specific binding of $^3$H-PRZ by 50%.

$IC_{50}$=(applied test substance concentration)

$$x \frac{1}{\left(\frac{C_o}{C_x}\right)} nM$$

where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| Compound | $IC_{50}$, nM | |
|---|---|---|
| | $^3$H—Oxo—M | $^3$H—Pz |
| 1 | 3.4 | 6.0 |
| 2 | 3.3 | 9.0 |
| 3 | 0.59 | 4.5 |
| 4 | 1.50 | 4.9 |
| 5 | 3.3 | 8.8 |
| 6 | 4.8 | 2.3 |
| 7 | 4.9 | 135.0 |
| 8 | 3.5 | 28.0 |
| 9 | 1.6 | 26.0 |
| 10 | 15.5 | 56.0 |
| 11 | 35 | |
| 12 | 63 | |
| 13 | 13 | |

The compounds of the invention, together with a conventional adjuvant, carrier, or diluent, and if desired in the form of a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, epntaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 1–100 mg in a pharmaceutically-acceptable carrier per unit dosage.

The dosage of the compounds according to this invention is 1–100 mg/day, preferably 10–70 mg/day, when administered to patients, e.g. humans, as a drug.

A typical tablet which may be prepared by conventional tabletting techniques contains:

| | | |
|---|---|---|
| Active compound | 5.0 mg | |
| Lactosum | 67.8 mg Ph.Eur. | |
| Avicel ® | 31.4 mg | |
| Amberlite ® | 1.0 mg | |
| Magnesii stearas | 0.25 mg Ph.Eur. | |

Due to the high muscarinic cholinergic receptor agonistic activity, the compounds of the invention are extremely useful in the treatment of symptoms related to a cholinergic deficit in the peripheral system. The compounds of the invention may accordingly be administered to a subject, e.g., a living animal body, including a human, in need of stimulation of the cholinergic system, and if desired in the form of a pharmaceutically acceptable salt (such as the hydrobromide, hydrochloride, or sulfate, in any event prepared in the usual or conventional manner) ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective stimulating amount, and in any event an amount which is effective for improving the symptoms related to a cholinergic deficit of mammals due to their muscarinic cholinergic receptor agonistic activity. Suitable dosage ranges are 1–100 milligrams daily, 10–100 milligrams daily, and especially 30–70 milligrams daily, depending as usual upon the exact mode of administration, form in which administered, the indication towards which the administration is directed, the subject involved and the body weight of the subject involved, and the preference and experience of the physician or veterinarian in charge.

The invention will now be described in further detail with reference to the following examples:

EXAMPLE 1

3-(3-Hexylthio-1,2,5-thiadiazol-4-yl)-1,2,5,6-tetrahydro-1,1-dimethylpyridinium iodide 3-(3-hexylthio-1,2,5-thiadiazol-4-yl)-1,2,5,6-tetrahydro-1-methylpyridine (0.59 g, 2 mmol) was dissolved in acetone (10 ml). Iodomethane (1.15 g, 8 mmol) was added, and the reaction mixture stirred for 2 h at room temperature. Ether (10 ml) was added. The precipitated title compound was filtered and dried. Yield: 0.5 g. M.p. 138–139° C. Compound 1.

EXAMPLE 2

In exactly the same manner the following compounds were made using the appropriate alkyl- halogenide:

3-(3-Hexyloxy-1,2,5-thiadiazol-4-yl)-1,2,5,6-tetrahydro-1,1-dimethylpyridinium iodide. M .p. 159–160° C. Compound 2.

3-(3-Ethoxy-1,2,5-thiadiazol-4-yl)-1,2,5,6-tetrahydro-1,1-dimethylpyridinium iodide. M.p. 235–236° C. Compound 3.

3-(3-Butylthio-1,2,5-thiadiazol-4-yl)-1-methyl-1-azabicyclo[2.2.2]octane iodide. M.p. 106–108° C. Compound 4.

Endo 6-(3-Butylthio-1,2,5-thiadiazol-4-yl)-1-methyl-1-azabicyclo[3.2.1]octane iodide. M.p. 179–180° C. Compound 5.

Endo 6-(3-Pentylthio-1,2,5-thiadiazol-4-yl)-1-methyl-1-azabicyclo[3.2.1]octane iodide. M.p. 164–166° C. Compound 6.

Exo 6-(3-Pentylthio-1,2,5-thiadiazol-4-yl)-1-methyl-1-azabicyclo[3.2.1]octane iodide. M.p. 130–132° C. Compound 7.

3-(3-Ethylthio-1,2,5-thiadiazol-4-yl)-1,2,5,6-tetrahydro-1-ethyl-1-methylpyridinium iodide. M.p. 153–154° C. Compound 8.

3-(3-Ethylthio-1,2,5-thiadiazol-4-yl)-1,2,5,6-tetrahydro-1,1-dimethylpyridinium iodide. M.p. 216–217° C. Compound 9.

3-(3-Ethoxy-1,2,5-thiadiazol-4-yl)-1,2,5,6-tetrahydro-1-ethyl-1-methyl-pyridinium iodide. M.p. 171–172° C. Compound 10.

Exo(+) 6-(3-(3-Thienyl)-2-propyn-1-yloxy)-1,2,5-thiadiazol-4-yl)-1-azabicyclo[3.2.1]-octane iodide. M.p. 153–155° C. Compound 11.

Exo(+) 6-(3-(3-(2-Thienyl)-2-propyn-1-yloxy)-1,2,5-thiadiazol-4-yl)-1-azabicyclo[3.2.1]-octane iodide. M.p. 122–124° C. Compound 12.

Exo(+) 6-(3-(3-Phenyl)-2-propyn-1-ylthio)-1,2,5-thiadiazol-4-yl)-1-azabicyclo[3.2.1]-octane iodide. M.p. 190–192° C. Compound 13.

What is claimed is:

1. A compound of formula I:

(I)

wherein
X is oxygen or sulfur,
G is:

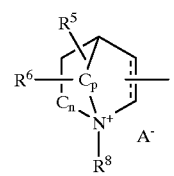

wherein the oxadiazole or thiadiazole ring is attached at any appropriate position; $R^5$ and $R^6$ are present at any appropriate position, and independently are H, straight or branched $C_{1-5}$-alkyl, straight or branched $C_{2-5}$-alkenyl, straight or branched $C_{2-5}$-alkynyl, straight or branched $C_{1-10}$-alkoxy, straight or branched hydroxyalkyl, —OH, halogen, —NH$_2$ or carboxy; R$^8$ is straight or branched $C_{1-5}$-alkyl, straight or branched $C_{2-5}$-alkenyl, straight or branched $C_{2-5}$-alkynyl, $C_{3-5}$-cycloalkyl or $C_{3-5}$-cycloalkyl-$C_{1-2}$-alkyl; n is 2; p is 1; . . . is a single bond or double bond; and A is a negative radical of a pharmaceutically acceptable salt;

R is hydrogen, halogen, —NR$^1$R$^2$, —R$^3$, —OR$^3$, —SR$^3$, —SOR$^3$, —SO$_2$R$^3$, $C_{3-8}$-cycloalkyl, $C_{4-12}$-(cycloalkylalkyl), —Z—$C_{3-10}$-cycloalkyl or —Z—$C_{4-12}$-(cycloalkylalkyl) wherein R$^1$ and R$^2$ independently are hydrogen or $C_{1-6}$-alkyl, and R$^3$ is straight or branched $C_{1-15}$-alkyl, straight or branched $C_{2-15}$-alkenyl, straight or branched $C_{2-15}$-alkynyl, or straight or branched $C_{4-15}$-alkenynyl, each of which is optionally substituted with one or more halogen(s), —CF$_3$, —CN, —OH, phenyl or phenoxy wherein the phenyl or phenoxy is optionally substituted with halogen, —OH, —CF$_3$, —CN, $C_{1-4}$-alkyl, $C_{1-4}$-alkoxy, $C_{1-4}$-alkylthio, —SCF$_3$, —OCF$_3$, —CONH$_2$ or —CSNH$_2$; or R is phenyl or benzyloxycarbonyl, each of which is optionally substituted with halogen, —OH, —CF$_3$, —CN, $C_{1-4}$-alkyl, $C_{1-4}$-alkoxy, $C_{1-4}$-alkylthio, —SCF$_3$, —OCF$_3$, —CONH$_2$ or —CSNH$_2$; or R is —OR$^4$Y, —SR$^4$Y, —OR$^4$ZY, —SR$^4$ZY, —OR$^4$ZR$^3$ or —SR$^4$ZR$^3$ wherein Z is oxygen or sulfur; R$^4$ is straight or branched $C_{1-15}$-alkylene, straight or branched $C_{2-15}$-alkenylene, straight or branched $C_{2-15}$-alkynylene or straight or branched $C_{4-15}$-alkenynylene; and Y is a [5 or 6-membered heterocyclic]thienyl group which is optionally substituted at carbon atom(s) with halogen, —OH, —CF$_3$, —CN, $C_{1-4}$-alkyl, $C_{1-4}$-alkoxy, $C_{1-4}$-alkylthio, —SCF$_3$, —OCF$_3$, —CONH$_2$, —CSNH$_2$, phenyl, benzyl or thienyl, or a carbon atom in the thienyl group together with an oxygen atom form a carbonyl group, or wherein the thienyl group is optionally fused with a phenyl group; or R is —R$^7$, —SOR$^7$ or —SO$_2$R$^7$ wherein R$^7$ is straight or branched $C_{1-15}$-alkyl, straight or branched $C_{2-15}$-alkenyl, straight or branched $C_{2-15}$-alkynyl, or straight or branched $C_{4-15}$-alkenynyl each of which is substituted with thienyl.

2. A compound of claim 1 wherein X is sulfur.

3. A compound of claim 2 wherein the thiadiazole is attached at the 3 position of G.

4. A compound of claim 1 wherein R is —OR$^4$Y or —SR$^4$Y and R$^4$ is (2-thienyl)-2-propyn-1-yl.

5. A compound of claim 1 wherein R is —OR$^4$Y or —SR$^4$Y and R$^4$ is (3-thienyl)-2-propyn-1-yl.

6. A compound of claim 2 wherein R$^5$ and R$^6$ are H.

7. A compound of claim 2 wherein R$^8$ is $C_{1-2}$-alkyl.

8. A compound of claim 2 wherein R is hydrogen, halogen, —NR$^1$R$^2$, —R$^3$, —OR$^3$, —SR$^3$, —SOR$^3$, —SO$_2$R$^3$, $C_{3-8}$-cycloalkyl, $C_{4-12}$-(cycloalkylalkyl), —Z—$C_{3-10}$-cycloalkyl or —Z—$C_{4-12}$-(cycloalkylalkyl) wherein R$^3$ is straight or branched $C_{1-15}$-alkyl, straight or branched $C_{2-15}$-alkenyl, or straight or branched $C_{2-15}$-alkynyl, or straight or branched $C_{4-15}$-alkenynyl, each of which is optionally substituted with one or more halogen(s), —CF$_3$, —CN, —OH, phenyl or phenoxy wherein the phenyl or phenoxy is optionally substituted with halogen, —OH, —CF$_3$, —CN, $C_{1-4}$-alkyl, $C_{1-4}$-alkoxy, $C_{1-4}$-alkylthio, —SCF$_3$, —OCF$_3$, —CONH$_2$ or —CSNH$_2$; or R is phenyl or benzyloxycarbonyl, each of which is optionally substituted with halogen, —OH, —CF$_3$, —CN, $C_{1-4}$-alkyl, $C_{1-4}$-alkoxy, $C_{1-4}$-alkylthio, —SCF$_3$, —OCF$_3$, —CONH$_2$ or —CSNH$_2$.

9. A compound of claim 8 wherein the thiadiazole is attached at the 3 position of G.

10. A compound of claim 8 wherein R$^5$ and R$^6$ are H.

11. A compound of claim 8 wherein R$^8$ is $C_{1-2}$-alkyl.

12. A compound of claim 8 wherein R is halogen, —OR$^3$, —SR$^3$ or —SO$_2$R$^3$ wherein R$^3$ is straight or branched $C_{1-15}$-alkyl, straight or branched $C_{2-15}$-alkenyl, straight or branched $C_{2-15}$-alkynyl, or straight or branched $C_{4-15}$-alkenynyl, each of which is optionally substituted with one or more halogen(s),—CF$_3$, —CN, —OH, phenyl or phenoxy wherein the phenyl or phenoxy is optionally substituted with halogen, —OH, —CF$_3$, —CN, $C_{1-4}$-alkyl, $C_{1-4}$-alkoxy, $C_{1-4}$-alkylthio, —SCF$_3$, —OCF$_3$, —CONH$_2$ or —CSNH$_2$.

13. A compound of claim 12 wherein R$^3$ is straight or branched $C_{1-15}$-alkyl, straight or branched $C_{2-15}$-alkenyl, straight or branched $C_{2-15}$-alkynyl or straight or branched $C_{4-15}$-alkenynyl, each of which is substituted with phenyl, wherein the phenyl is optionally substituted with halogen(s), —CN, $C_{1-4}$-alkyl, $C_{1-4}$-alkoxy, $C_{1-4}$-alkylthio, —SCF$_3$ or —OCF$_3$.

14. A compound of claim 13 wherein R is —OR$^3$ or —SR$^3$, wherein R$^3$ is propynyl substituted with phenyl wherein the phenyl is optionally substituted with halogen(s), —CN, $C_{1-4}$-alkyl, $C_{1-4}$-alkylthio, —SCF$_3$ or —OCF$_3$.

15. A compound of claim 14 wherein R$^3$ is (3-Phenyl)-2-propyn-1-yl.

16. A compound of claim 1 which is a pharmaceutically acceptable salt of:

Endo 6-(3-Butylthio-1,2,5-thiadiazol-4-yl)-1-methyl-1-azabicyclo[3.2.1]octane,

Endo 6-(3-Butylthio-1,2,5-thiadiazol-4-yl)-1-methyl-1-azabicyclo[3.2.1]octane, or Exo 6-(3-Pentylthio-1,2,5-thiadiazol-4-yl)-1-methyl-1-azabicyclo[3.2.1]octane.

17. A compound of claim 1 which is a pharmaceutically acceptable salt of:

Exo(+)6-(3-(3-(3-Thienyl)-2-propyn-1-yloxy)-1,2,5-thiadiazol-4-yl)-1-azabicyclo[3.2.1]octane, or Exo(+)6-(3-(3-(2-Thienyl)-2-propyn-1-yloxy)-1,2,5-thiadiazol-4-yl)-1-azabicyclo[3.2.1]octane.

18. A compound of claim 1 which is a pharmaceutically acceptable salt of:

Exo(+)6-(3-(3-(3-Phenyl)-2-propyn-1-ylthio)-1,2,5-thiadiazol-4-yl)-1-azabicyclo[3.2.1]octane.

19. A pharmaceutical composition comprising a compound of claim 1 together with a pharmaceutically acceptable carrier or diluent.

20. The pharmaceutical composition comprising a compound of claim 19 in the form of an oral or parenteral dosage unit.

21. The pharmaceutical composition comprising a compound of claim 20, wherein the dosage unit comprises from about 0.1 to about 100 mg of the compound.

22. A pharmaceutical composition comprising a compound of claim 21 together with a pharmaceutically acceptable carrier or diluent.

23. A pharmaceutical composition comprising a compound of claim 8 together with a pharmaceutically acceptable carrier or diluent.

24. A pharmaceutical composition comprising a compound of claim 13 together with a pharmaceutically acceptable carrier or diluent.

* * * * *